United States Patent
Rémigy

(10) Patent No.: US 9,772,265 B2
(45) Date of Patent: Sep. 26, 2017

(54) PREPARATION OF SAMPLE FOR CHARGED-PARTICLE MICROSCOPY

(71) Applicant: FEI Company, Hillsboro, OR (US)

(72) Inventor: Hervé-William Rémigy, Eindhoven (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 15/052,313

(22) Filed: Feb. 24, 2016

(65) Prior Publication Data

US 2016/0245732 A1    Aug. 25, 2016

(30) Foreign Application Priority Data

Feb. 25, 2015  (EP) .................................. 15156546

(51) Int. Cl.
  *H01J 37/26*  (2006.01)
  *H01J 37/20*  (2006.01)
  (Continued)

(52) U.S. Cl.
  CPC ............. *G01N 1/2813* (2013.01); *G01N 1/42* (2013.01); *H01J 37/20* (2013.01); *H01J 37/26* (2013.01);
  (Continued)

(58) Field of Classification Search
  CPC ........ H01J 37/20; H01J 37/26; G01N 1/2813; G01N 1/42; G01N 1/20; G01N 1/31
  (Continued)

(56) References Cited

U.S. PATENT DOCUMENTS

| 8,757,873 B2 * | 6/2014 | van den Boom | ........ G01K 5/68 374/100 |
| 9,116,091 B2 * | 8/2015 | Remigy | .................... F25D 3/11 |

(Continued)

FOREIGN PATENT DOCUMENTS

| EP | 2853847 A1 | 4/2015 |
| EP | 3032564 A1 | 6/2016 |

OTHER PUBLICATIONS

"Electron Microscope",Wikipedia, Retrieved from the Internet Oct. 15, 2015 from http://en.wikipedia.org/wiki/Electron_microscope, 11 pgs.

(Continued)

*Primary Examiner* — David A Vanore
(74) *Attorney, Agent, or Firm* — Scheinberg & Associates, P.C.; Michael O. Scheinberg

(57) ABSTRACT

A system and method for preparing a sample for study in a charged-particle microscope is disclosed. A sample holder comprises substantially parallel opposing faces connected by apertures spanned by a perforated membrane. Blotting material is placed against the outer membrane surface, and liquid films may then be deposited onto the inner membrane surface within each aperture where each aperture can contain a unique sample. Liquids from each sample flow through the perforations in the membrane to be absorbed by the blotting material. After completion of deposition of liquid samples, the sample holder is raised off the blotting material, leaving aqueous samples within the perforations of the membrane. The sample holder may then be immersed in a vitrifying bath of liquid oxygen to form a cryo-sample for microscopic imaging and analysis.

18 Claims, 5 Drawing Sheets

Figure 1:
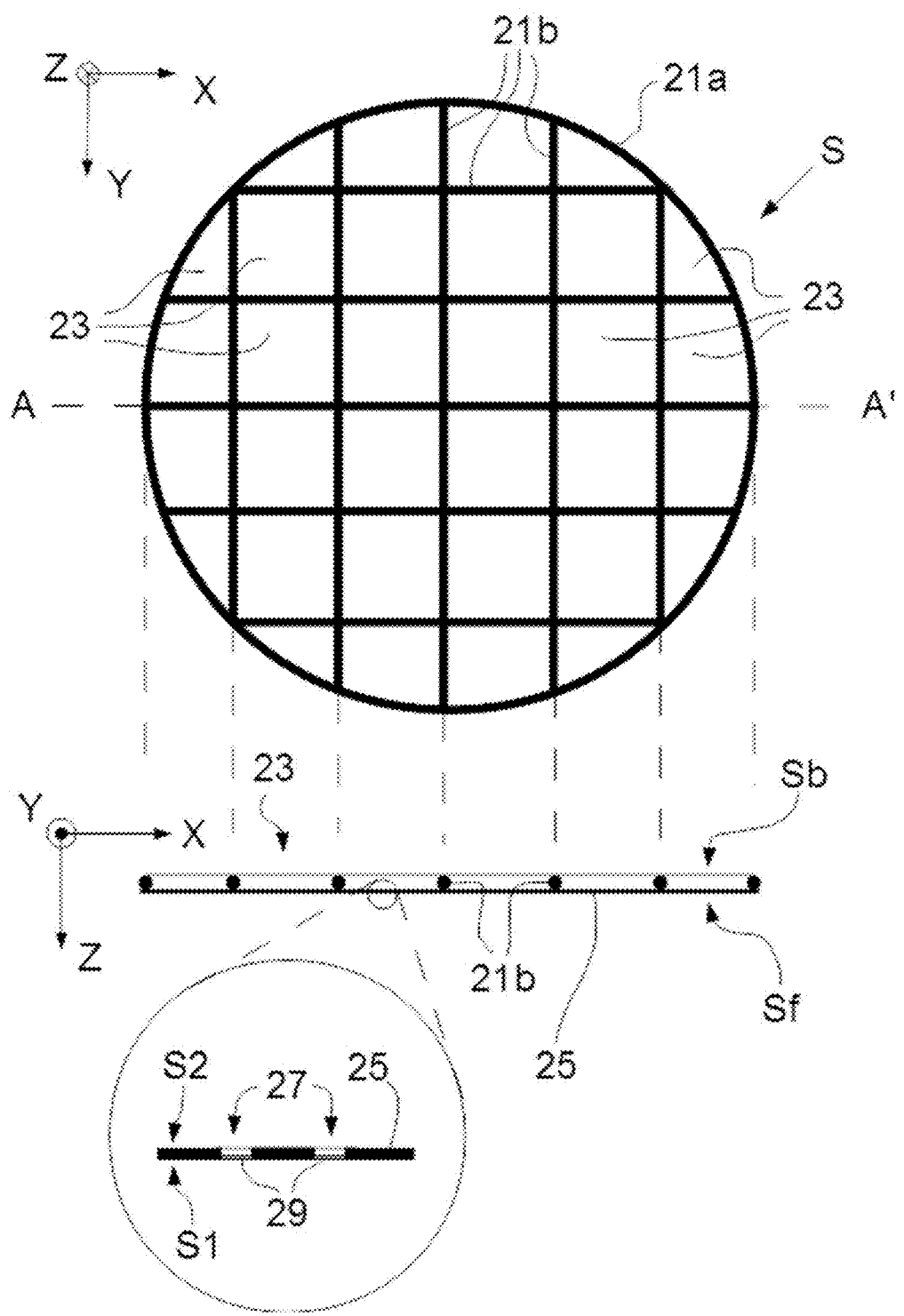

(51) Int. Cl.
  *G01N 1/28* (2006.01)
  *G01N 1/42* (2006.01)
(52) U.S. Cl.
  CPC . *H01J 2237/002* (2013.01); *H01J 2237/2001* (2013.01); *H01J 2237/208* (2013.01)
(58) Field of Classification Search
  USPC .................................. 250/307; 374/100, 159
  See application file for complete search history.

(56) References Cited

U.S. PATENT DOCUMENTS

2015/0090878 A1* 4/2015 Remigy ................... F25D 3/11
  250/307
2016/0245732 A1* 8/2016 Remigy ................... G01N 1/42

OTHER PUBLICATIONS

"Scanning Electron Microscope", Wikipedia. Retrieved from the Internet Oct. 15, 2015, http://en.wikipedia.org/wiki/Scanning_electron_microscope, 23 pages.

"Scanning Helium Ion Microscope".Wikipedia, Retrieved from the Internet on Oct. 15, 2015, http://en.wikipedia.org/wiki/Scanning_Helium_Ion_Microscope, 2 pages.

"Scanning Transmission Electron Microscopy", Wikipedia, Retrieved from the Internet Oct. 15, 2015, http://en.wikipedia.org/wiki/Scanning_transmission_electron_microscopy, 5 pages.

"Transmission Electron Microscopy", Wikipedia, Retrieved from the Internet Oct. 15, 2015, http://en.wikipedia.org/wiki/Transmission_electron_microscopy, 23 pages.

Burrows, N. et al., "Cryogenic Transmission Electron Microscopy: Aqueous Suspensions of Nanoscale Objects," Microscopy and Microanalysis, 2013, pp. 1542-1553, vol. 19, No. 6.

Escovitz W.H. et al, "Scanning Transmission Ion Microscope with a Field Ion Source," Proc. Nat. Acad. Sci. USA, May 1975, pp. 1826-1828, vol. 72, No. 5.

Melanson, L. "Cryo TEM from specimen prep to the microscope," Cryo TEM Workshop Baylor College of Medicine, Retrieved from the internet Dec. 22, 2014, www.stehm.uvic.ca/facility/instruments/Cryoplunge3/Gatan_CryoTEM_presentation.pdf, 34 pages.

* cited by examiner

PREPARATION OF SAMPLE FOR CHARGED-PARTICLE MICROSCOPY

The invention relates to a method of preparing a sample for study in a charged-particle microscope, comprising the following steps:

Providing a substantially planar sample holder having opposed faces substantially parallel to one another, comprising at least one aperture that connects said faces and across which a membrane has been mounted, which membrane comprises at least one perforation;

Spanning a film of aqueous liquid across said perforation, which liquid comprises at least one study specimen suspended therein.

The invention also relates to a method of examining a sample in a charged-particle microscope (CPM), which microscope comprises:

A supporting device, for supporting a sample holder on which the sample is mounted;

A charged-particle source, for producing a beam of charged particles;

An illuminator, for directing said beam so as to irradiate the sample;

A detector, for detecting a flux of output radiation emanating from the sample in response to said irradiation.

In general, after preparation and prior to examination in a CPM, a sample of a type as referred to above will be solidified/rapidly frozen/vitrified, e.g. by plunging it into a bath of cryogen, and then removing it from the bath and maintaining it at cryogenic temperatures during transport/storage.

As used throughout this text, the ensuing terms should be interpreted consistent with the following explanation:

The substantially planar sample holder may comprise more than one of the described apertures; in particular, it may be a grid-like structure that contains a matrix arrangement of such apertures. Similarly, the membrane spanned across a given aperture may contain more than one of the described perforations; in particular, it may comprise a (random or regular) distribution of such perforations. The perforations themselves may be deliberately created (e.g. using a boring, pricking, punching or etching technique), or they may be naturally present in the membrane. In the current context, the sample holder may be regarded as a "scaffolding" that serves to support the thin membrane mounted (stretched) thereon. Pre-manufactured, disposable, grid-like sample holders as described here are commercially available, e.g. in the form of so-called "TEM grids" or "autogrids". Similarly, perforated membranes are also commercially available, e.g. in the form of so-called "holey carbon" or Quantifoil® membranes.

The phrase "aqueous liquid" is intended to encompass pure liquid water, but also water-based solutions or suspensions. The term therefore includes electrolytes, in addition to biological liquids such as cytoplasm, blood plasma, lymphatic fluid or amniotic fluid, for example. This aqueous liquid film is essentially "spanned" across said perforation(s) with the aid of surface tension effects.

The term "cryogen" should be interpreted as referring to a liquid at cryogenic temperatures, i.e. at or below −150° C.

The "sample" in the current case may be regarded as being said spanned film of (solidified/vitrified) aqueous liquid, including its suspended study specimen(s). In practice, a CPM study performed on such a sample will generally tend to concentrate on said specimen(s) rather than on the (solidified) liquid in which they are encapsulated.

Charged particle microscopy is a well-known and increasingly important technique for imaging microscopic objects, particularly in the form of electron microscopy. Historically, the basic genus of electron microscope has undergone evolution into a number of well-known apparatus species, such as the Transmission Electron Microscope (TEM), Scanning Electron Microscope (SEM), and Scanning Transmission Electron Microscope (STEM), and also into various sub-species, such as so-called "dual-beam" tools (e.g. a FIB-SEM), which additionally employ a "machining" Focused Ion Beam (FIB), allowing supportive activities such as ion-beam milling or Ion-Beam-Induced Deposition (IBID), for example. More specifically:

In a SEM, irradiation of a sample by a scanning electron beam precipitates emanation of "auxiliary" radiation from the sample, in the form of secondary electrons, backscattered electrons, X-rays and photoluminescence (infrared, visible and/or ultraviolet photons), for example; one or more components of this flux of emanating radiation is/are then detected and used for image accumulation purposes.

In a TEM, the electron beam used to irradiate the sample is chosen to be of a high-enough energy to penetrate the sample (which, to this end, will generally be thinner than in the case of a SEM sample); the flux of transmitted electrons emanating from the sample can then be used to create an image. When such a TEM is operated in scanning mode (thus becoming a STEM), the image in question will be accumulated during a scanning (e.g. raster or serpentine) motion of the irradiating electron beam.

More information on some of the topics elucidated here can, for example, be gleaned from the following Wikipedia links:

http://en.wikipedia.org/wiki/Electron_microscope http://en.wikipedia.org/wiki/Scanning_electron_microscope http://en.wikipedia.org/wiki/Transmission_electron_microscopy http://en.wikipedia.org/wiki/Scanning_transmission_electron_microscopy As an alternative to the use of electrons as irradiating beam, charged particle microscopy can also be performed using other species of charged particle. In this respect, the phrase "charged particle" should be broadly interpreted as encompassing electrons, positive ions (e.g. Ga or He ions), negative ions, protons and positrons, for instance. As regards ion-based microscopy, some further information can, for example, be gleaned from sources such as the following:

http://en.wikipedia.org/wiki/Scanning_Helium_Ion_Microscope

W. H. Escovitz, T. R. Fox and R. Levi-Setti, *Scanning Transmission Ion Microscope with a Field Ion Source*, Proc. Nat. Acad. Sci. USA 72(5), pp. 1826-1828 (1975).

It should be noted that, in addition to imaging, a charged particle microscope may also have other functionalities, such as performing spectroscopy, examining diffractograms, performing (localized) surface modification (e.g. milling, etching, deposition), etc.

In all cases, a Charged Particle Microscope (CPM) will comprise at least the following components:

A radiation source, such as a Schottky electron source or ion gun.

An illuminator, which serves to manipulate a "raw" radiation beam from the source and perform upon it certain operations such as focusing, aberration mitigation, cropping (with an aperture), filtering, etc. It will generally comprise one or more (charged-particle) lenses, and may comprise other types of (particle-) optical component also. If desired, the illuminator can be provided with a deflector system that can be invoked to cause its output beam to perform a scanning motion across the sample being investigated.

A supporting device, on which a sample holder/sample under investigation can be held and positioned (e.g. tilted, rotated). If desired, this supporting device can be moved so as to effect scanning motion of the beam w.r.t. the sample. In general, such a supporting device will be connected to a positioning system such as a mechanical stage, for example.

A detector, which may be unitary or compound/distributed in nature, and which can take many different forms, depending on the radiation being detected (in response to irradiation of a sample). Examples include photomultipliers (including solid state photomultipliers, SSPMs), photodiodes, CMOS detectors, CCD detectors, photovoltaic cells, etc., which may, for example, be used in conjunction with a scintillator film, for instance. For X-ray detection, use is typically made of a so-called Silicon Drift Detector (SDD), or a Silicon Lithium (Si(Li)) detector, for example. Typically, a CPM will comprise several detectors, of various types.

In the case of a transmission-type microscope (such as a (S)TEM, for example), the CPM will also comprise:

An imaging system, which essentially takes charged particles that are transmitted through a sample (plane) and directs (focuses) them onto analysis apparatus, such as a detection/imaging device, spectroscopic apparatus (such as an EELS module; EELS=Electron Energy-Loss Spectroscopy), etc. As with the illuminator referred to above, the imaging system may also perform other functions, such as aberration mitigation, cropping, filtering, etc., and it will generally comprise one or more charged-particle lenses and/or other types of particle-optical components.

In what follows, the invention may—by way of example—sometimes be set forth in the specific context of electron microscopy. However, such simplification is intended solely for clarity/illustrative purposes, and should not be interpreted as limiting.

The examination of certain types of sample in a CPM can present significant challenges as regards their preparation, transport and handling. In particular, biological specimens (such as cells, cell components, single-cellular organisms, etc.) that need to be stored and studied in a body of aqueous liquid (such as water, electrolyte, cell fluid, blood plasma, etc.) can be difficult to work with, since:

An aqueous liquid introduced into a (quasi-)vacuum environment of a CPM will start to outgas/boil, thus tending to degrade the sample.

In order to prevent this, the sample is typically frozen/solidified before being introduced into said vacuum.

However, so as to prevent damage to the sample caused by the formation of (sharp) ice crystals, such freezing must generally be performed very rapidly, with the aim of achieving sample vitrification (solidification into an amorphous, glass-like phase) without significant ice crystallization. Such vitrification is typically achieved by rapidly plunging the sample into a cryogen bath.

To facilitate acceptable vitrification, the sample should preferably have a relatively large surface-area-to-volume ratio. Moreover, if the sample is to be subsequently examined in a transmission-type CPM (such as a (S)TEM), then the irradiating charged-particle beam must be able to penetrate the sample, and enter an imaging system downstream of the sample. These demands require the sample to be relatively thin, and to be mounted on a sample holder that does not appreciably interfere with (occlude) the nominal path of said beam—which essentially requires the sample to be supportable by/along its edges.

To meet these requirements, aqueous samples of this type are typically prepared as thin films that are spanned (on the basis of surface tension effects) across/within small perforations (openings) in a thin membrane, somewhat analogous to the way in which a soapy film spans itself across the ring of a bubble blower. One known way to achieve such spanning is to wet the sample holder with some of the aqueous liquid—e.g. by immersing it in a dish of such liquid, or dropping the liquid onto it with a pipette—and then briefly pressing a sheet of blotting paper intimately against a face of the sample holder. Such blotting serves to remove excess liquid from the sample holder, with the aim of leaving a more uniform layer of liquid behind on the sample holder when the blotting paper is removed. A method of this type is, for example, set forth in the publication *Single Cell Analysis: Technologies and Applications*, edited by Dario Anselmetti, Wiley VCH publishers, 2009, ISBN 978-3-527-31864-3, particularly §3.2, pages 44 and 45: https://books.google.nl/books?isbn=3527626654

Although the technique set forth in the previous paragraph has produced tolerable results up to now, the current inventors have worked extensively to improve upon the conventional approach. The results of this endeavor are the subject of the current invention.

It is an object of the invention to provide an improved method of sample preparation. In particular, it is an object of the invention that this improved method should be more versatile and efficient than known methods, and that it should produce a better-quality sample than prior-art approaches.

These and other objects are achieved in a method as set forth in the opening paragraph above, which method is characterized by the following steps:

Prior to said spanning step, placing a blotting sheet of blotting material in intimate contact with a first surface of said membrane, at a side distal from said sample holder;

Depositing said aqueous liquid through said aperture and onto a second surface of said membrane, opposite said first surface;

Subsequently removing said blotting sheet from said membrane.

This method differs from the prior art inter alia in that:

The blotting sheet is applied to the sample holder prior to (rather than after) the depositing step;

The depositing step occurs from the side of the membrane (second surface) opposite the side to which the blotting sheet is applied (first surface);

The depositing step occurs through the aperture (grid), so that it can be regarded as "backside deposition" rather than "frontside deposition".

These (and other) differences will be discussed in more detail below.

In experiments leading to the invention, the inventors made a number of important observations, as follows:

Post-application of blotting paper to a membrane that has already received a deposit of aqueous liquid can cause mechanical damage to delicate specimens (such as biological cells) present in the liquid.

The liquid layer left behind on the sample holder after post-deposition blotting is relatively irregular in thickness, leading to relatively poor thickness uniformity of the portions of this layer present in the membrane perforations (i.e. the spanned films that will undergo subsequent study in a CPM).

"Blanket" deposition of liquid on the sample holder (prior to application of blotting paper) is a relatively inefficient process, since most of the liquid will settle outside rather than inside the perforations in the membrane. If the concentration of floating specimens in the aqueous liquid is relatively low, then such inefficiency can lead to loss of valuable/rare specimens.

In contrast, pre-deposition application of a blotting sheet (comprising paper or cloth, for example) in accordance with the present invention mitigates the mechanical damage issue referred to above. Moreover, since the inventive method performs deposition from one side of the membrane and blotting from the other side, the perforation(s) in the membrane is/are more uniformly filled with liquid, leading to creation of a more uniform spanned film. The inventors have observed that, as soon as aqueous liquid within a perforation touches the pre-placed blotting sheet, it forms a thin surface film of liquid on the blotting sheet, which is observed to have a high hydrophilicity and thus serves to "draw" liquid into the perforation from the deposition side of the membrane.

In a particular embodiment of the invention, the following applies:

Said membrane comprises multiple perforations, and is mounted across a plurality of said apertures such that at least one perforation occurs within each aperture of said plurality;

Said depositing step is localized, and is confined to a particular zone of the sample holder, which zone comprises a subset of said plurality of apertures.

A great advantage of the invention is that it allows localized deposition of aqueous liquid on the sample holder, as opposed to the "blanketing" or "global" deposition that occurs in prior-art techniques. To facilitate discussion of this point, a (non-limiting) example will be considered of a grid-like sample holder comprising a matrix arrangement of apertures (cells) that are defined by thin wire "retaining walls", on one side/face ("frontside") of which grid a perforated membrane has been stretched, whereby at least one (and typically several) perforations is/are present within the confines of any given aperture. Because the inventive method performs "backside" liquid deposition through the apertures of the grid, the retaining walls of each aperture act as lateral flow barriers to the liquid, curtailing its spread into neighboring apertures. Consequently, if the liquid is deposited from a relatively narrow, well-defined source (see discussion below), then one can confine deposition to a given "zone" of the sample holder, which zone (according to choice) comprises one or more (but not all) of the apertures in the sample holder. This allows a sample to be prepared using considerably less aqueous liquid than in the case of prior-art "blanketing" deposition. In addition, it opens the way for an embodiment as set forth in the next paragraph.

In a special case of the embodiment just described, the inventive method is characterized in that, before removing said blotting sheet, said depositing step is performed in at least two different zones of the sample holder, whereby:

A first aqueous liquid is deposited through a first aperture in a first of said zones;

A second aqueous liquid, different from said first aqueous liquid, is deposited through a second aperture in a second of said zones.

The lateral confinement described in the previous paragraph—whereby the retaining walls of the apertures in the sample holder serve to confine deposited liquid to a given zone—allows multiple (mutually exclusive and/or partially overlapping) zones to be created on the sample holder, each comprising a different aqueous liquid. In this way, multiple samples can be deposited on a single sample holder—which thus greatly simplifies sample handling, in that it is no longer necessary to load/unload and positionally calibrate a separate sample holder for each different type of sample to be investigated, thereby streamlining operations, saving time and reducing contamination risks and required sample storage space. This is particularly (but not exclusively) advantageous in comparative sample studies, in which, for example, a given type of study specimen (e.g. a particular type of virus) has been subjected to different influences (e.g. exposure to different types of anti-viral substance, radiation, growth conditions, etc.) and one wishes to compare the effects that these have had on the specimen. In the present embodiment, such samples can be deposited at (zones with) different coordinate positions on a single sample holder, and one can easily move from one coordinate position to another to compare observations, without having to constantly switch to (and wait for loading of) different sample holders.

In a particular embodiment of the invention, said depositing step is performed using a dispensing device selected from the group comprising a contactless dispenser and a touch-off dispenser. Such dispensers have the advantage of allowing (very) localized deposition of aqueous liquid, if desired, but they can also be used to deposit liquid on relatively large areas, e.g. by employing a scanning motion of their dispensing "head" relative to the sample holder. It should hereby be noted that:

An example of a contactless dispenser in the current context is an inkjet-type dispenser, which can be used to controllably fire a well-aimed train of small droplets at a target location. Another example is a so-called "continuous flow dispenser" (or "volumetric dispenser"), which produces a continuous fine stream of liquid (from a very narrow nozzle) rather than a discrete burst of droplets.

In the case of a touch-off dispenser, a droplet of liquid at the end of a pin is touched against—and "rubbed off" onto—a sample holder by using viscosity/adhesion/surface tension effects to transfer ("pull") the droplet from source to destination.

When one wishes to deposit different aqueous liquids onto different zones of the sample holder (see above), then one can, for example:

Use a different dispenser for each different liquid; or

Use the same dispensing head/nozzle/capillary/pin in conjunction with different reservoirs/storage vessels for the various different liquids, or supply of the different liquids serially through a single supply line/tube with a suitable "separator" (such as a small quantity ("plug") of DiMethyl SulfOxide (DMSO), for example) between successive/consecutive bodies of liquid.

The skilled artisan will be well able to choose/adapt a particular dispensing technique according to the requirements of a given situation.

In another embodiment of the invention, at least said depositing step is performed in a space (enclosure/chamber/ room) having a relative humidity (RH) of at least 95%. A relatively high aerial humidity helps to prevent drying out of the sample during sample preparation (prior to vitrification), particularly in a situation in which different zones of the sample holder are provided with different aqueous liquids—which typically consumes more time than deposition of just one type of aqueous liquid. Such relatively high RH levels—which may preferably exceed 95%—can, for example, be achieved/maintained using a humidifier.

In a particular embodiment of the invention, the blotting sheet is pre-wetted prior to said depositing step. It has already been stated above that, when the blotting sheet is moistened, its hydrophilicity helps draw the deposited aqueous liquid through the perforation(s) from the deposition side (backside). Instead of waiting for the blotting sheet to become moistened by the deposited aqueous liquid itself, one can "kick start" this process by pre-wetting the blotting sheet prior to the depositing step. Such pre-wetting can occur before or after placing the blotting sheet against the membrane; in the latter case, one could, for example, use a spray to moisten the exposed surface of the blotting sheet that points away from the membrane. Pre-wetting can occur with pure water, or with a water-based solution/suspension that does not have a detrimental effect on the aqueous liquid that will subsequently be deposited; in that respect, pre-wetting can, if desired, be performed with the same type of aqueous liquid as will subsequently be deposited. Pre-wetting the blotting sheet in this manner also helps to maintain an elevated RH in the vicinity of the sample holder (see previous paragraph).

When the depositing step in the inventive method has been completed, the blotting sheet can be removed (e.g. peeled or slid) from the sample holder, leaving behind a thin film of aqueous liquid in the perforation(s) of the membrane. Typically, the sample holder (+aqueous liquid sample(s) thereon) will then be plunge-cooled by dipping it into a cryogen such as liquid ethane (e.g. at a temperature in the range −160° C. to −183° C.). A description of such a plunge-cooling process is, for example, contained in European Patent Application EP 13186632 (FNL1320) [incorporated herein by reference]. Once the sample holder has been plunge-cooled in this manner, it should be stored/transported at cryogenic temperatures, to maintain the sample(s) thereon in a vitrified state. A description of a so-called cryo-transfer holder suitable for use in this context is for example, contained in European Patent Application EP 14197422 (FNL1423) [incorporated herein by reference].

As a general matter, the skilled artisan will understand that a sample prepared according to the current invention can, in principle, also be investigated in apparatus other than a CPM, e.g. in an X-Ray diffractometer (for crystallography studies, for instance).

The invention will now be elucidated in more detail on the basis of exemplary embodiments and the accompanying schematic drawings, in which:

FIG. 1 renders a plan view (top), transverse cross-sectional view (middle) and enlarged detail view (bottom) of aspects of a particular embodiment of a sample holder that can be used to bear a sample comprising a film of aqueous liquid, and that can be prepared using a method according to the present invention.

FIGS. 2A-2E show a sample holder such as that depicted in FIG. 1, during execution of various steps of an embodiment of a method according to the present invention.

Figure 3:
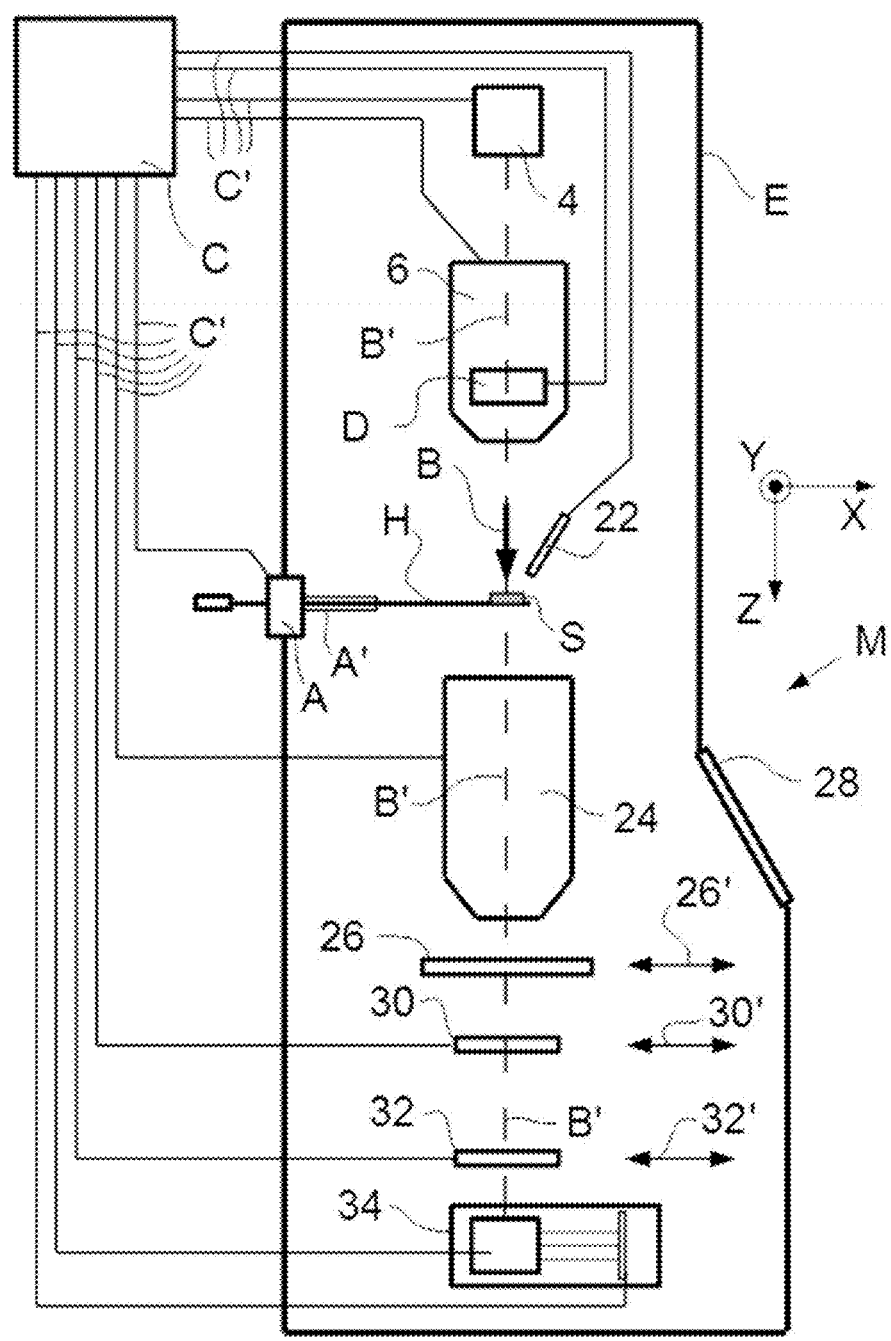

FIG. 3 renders an elevational view of a charged-particle microscope that lends itself to use with the current invention.

In the Figures, where pertinent, corresponding parts may be indicated using corresponding reference symbols. It should be noted that, in general, the Figures are not to scale.

EMBODIMENT 1

FIG. 1 (not necessarily to scale) renders various views of aspects of a particular embodiment of a sample holder S that can be used in conjunction with the current invention This particular type of sample holder S comprises what is often referred to as a "grid" or "autogrid". It comprises a circular ring 21a of Cu (or other metal) wire, the diameter of the ring being ca. 3 mm and the diameter of the wire being of the order of about 50-100 μm (typically). Located/attached within the ring 21a are straight wire portions 21b, which are arranged to form an orthogonal grid pattern, thus defining a matrix-like array of (substantially square) apertures (openings/holes/windows) 23. The middle portion of FIG. 1 shows a transverse cross-sectional view of the upper portion of the Figure, taken along the diameter A-A'. It shows that the sample holder S has a substantially planar (flat/plate-like) form, with opposed "front" (Sf) and "back" (Sb) faces substantially parallel to one another. Any given aperture 23 "connects" these faces Sb, Sf in that it acts as a connecting passage between them.

As here depicted, a membrane 25 has been mounted (laid, stretched) upon the front face Sf (and, optionally, affixed to the wires 21b, e.g. using an adhesive or by molten bonding). This membrane 25 may, for example, comprise a carbonaceous material such as nylon or graphene, and will typically have a thickness (in the Z direction) ranging from about 0.3 nm to hundreds of nm. The membrane 25 contains a distribution of perforations 27, which are clearly visible in the detailed view at the bottom of the Figure. These perforations 27 typically have a diameter/width (parallel to the XY plane) of the order of about 2 μm. Note that the membrane 25 has:

A first surface S1, which faces away from the grid 21a, 21b;

A second surface S2, which faces toward the grid 21a, 21b.

In essence, the grid structure 21a, 21b acts as a scaffold for the membrane 25, and the membrane 25 in turn acts as a supporting structure for the perforations 27 (so that it is sometimes referred to as a "holey carbon support"). It is within the perforations 27 that the ultimate "sample" is to be provided and supported—in the form of a thin film 29 of aqueous liquid (comprising one or more study specimens suspended therein) that is spanned across each given perforation 27, remaining in place (inter alia) by virtue of surface tension effects.

It should be noted that sample holders S as depicted in FIG. 1 (grid 21a, 21b+perforated membrane 25, 27) and as described above are commercially available, e.g. from firms such as Ted Pella, Inc., of Redding, Calif., USA. It is also possible to purchase (a variety of) pre-manufactured holey carbon films (corresponding to the perforated membrane 25, 27), e.g. from firms such as Quantifoil Micro Tools GmbH, Jena, Germany. It should be noted that, in principle, a sample holder S for use in the current invention basically requires only one aperture 23 and only one perforation 27; however, a plurality of these structures 23, 27 is certainly allowed by the invention, and is generally advantageous in that it typically allows more sample material to be present on a given area of the sample holder S.

EMBODIMENT 2

Figure 2A:
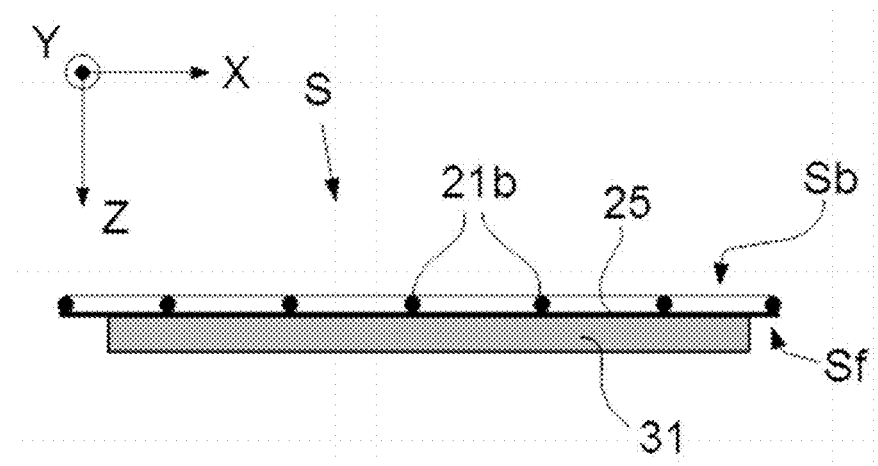

FIGS. 2A-2E show a sample holder S such as that depicted in FIG. 1, during execution of various steps of an embodiment of a method according to the present invention. In particular, the following is depicted:

FIG. 2A: Prior to deposition of aqueous liquid on the membrane 25, a blotting sheet 31 of blotting material (e.g. Whatman Paper no. 1) is placed in intimate contact with first surface S1 of the membrane 25 (which surface S1 is distal from grid wires 21b). This blotting sheet 31 may be dry or pre-wetted, as desired.

Figure 2B:
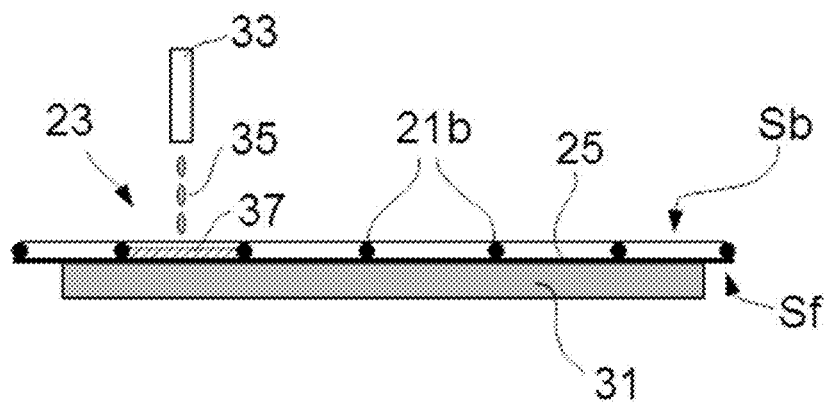

FIG. 2B: Using a dispensing device 33 (such as an inkjet-type nozzle), a stream/train of droplets of aqueous liquid 35 is locally deposited onto the second surface S2 of membrane 25, forming a "pool" 37 of liquid. This occurs from the back side Sb of the holder S, through aperture 23. The grid wires 21b along the perimeter of aperture 23 contain the pool 37 laterally, thus confining spread in the XY plane. Typically, a dose of the order of ca. 20 nanoliters (for example) may be deposited in this way in aperture 23.

Figure 2C:
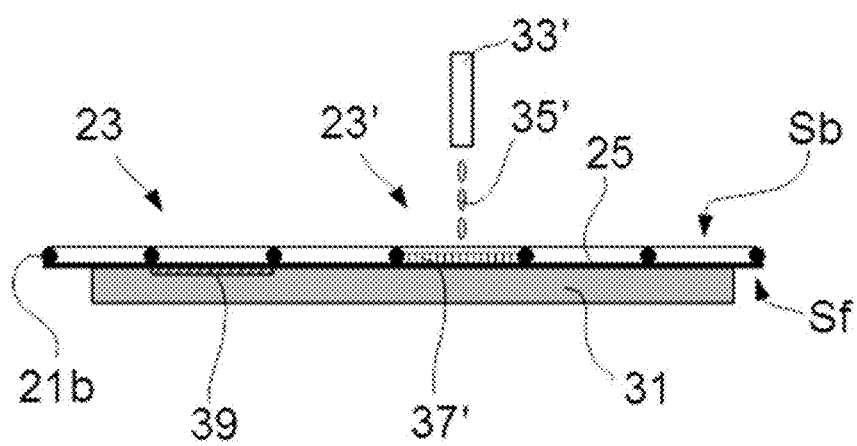

FIG. 2C: Here, the procedure performed in FIG. 2B is being repeated at a different aperture 23'. As shown here, this is being done with a different aqueous liquid 35', deposited from a different dispensing device 33'; however, as explained above, it is also possible to use the same device 33 as in FIG. 2B, if desired. Note that the pool 37 initially present in aperture 23 (FIG. 2B) has started to soak into blotting sheet 31, forming a blotted patch 39. If desired, procedures such as those shown in FIGS. 2B and 2C may be repeated at other apertures. In addition, if desired, after performing deposition in a given aperture, prior depositions in other apertures may be "topped up" before moving on to the next major step (blotting sheet removal); generalizing, the deposition procedure in one or more apertures may be a multi-step process, if desired.

Figure 2D:
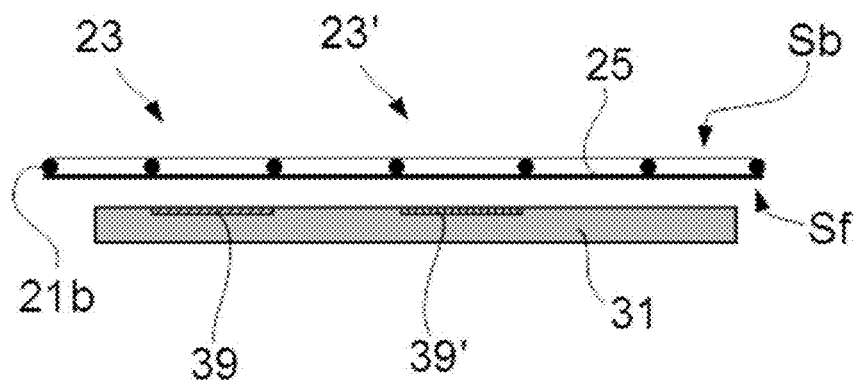

FIG. 2D: The deposition step has been completed, and blotting sheet 31 has been removed (e.g. peeled, slid, stripped) from the membrane 25. Note the blotted patch 39' that has formed as a result of blotting of the pool 37' out of aperture 23'.

Figure 2E:
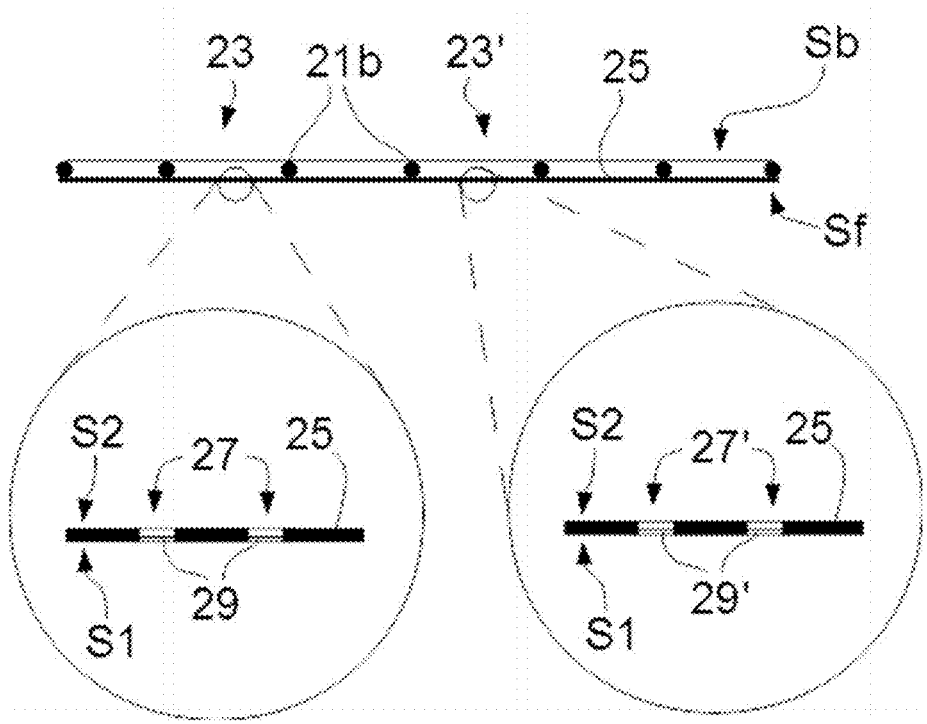

FIG. 2E: After removal of the blotting sheet 31, thin films 29, 29' of aqueous liquids 35, 35' (respectively) have been left behind in the perforations 27, 27' within apertures 23, 23' (respectively).

After removal of the blotting sheet 31, the sample holder S can be plunged into a vitrifying bath of cryogen.

EMBODIMENT 3

FIG. 3 is a highly schematic depiction of an embodiment a CPM in which the current invention can be applied; more specifically, it shows an embodiment of a transmission-type microscope M, which, in this case, is a TEM/STEM (though, in the context of the current invention, it could just as validly be an ion-based microscope, and/or a non-transmission type microscope such as a SEM, for example). In the Figure, within a vacuum enclosure E, an electron source 4 (such as a Schottky emitter, for example) produces a beam (B) of electrons that traverse an electron-optical illuminator 6, serving to direct/focus them onto a chosen part of study object S; although a large variety of different types of study object S can be investigated in a (S)TEM, it will be assumed in the current context that the study object S is a sample holder S prepared according to the current invention, e.g. as set forth in Embodiment 2 (comprising vitrified aqueous film 29). This illuminator 6 has an electron-optical axis B', and will generally comprise a variety of electrostatic/magnetic lenses, (scan) deflector(s) D, correctors (such as stigmators), etc.; typically, it can also comprise a condenser system (in fact, the whole of item 6 is sometimes referred to as "a condenser system").

The sample holder S is held on a (rod-like) supporting device H that seats into a cradle A' (such as the FEI CompuStage) connected to a positioning device (stage, actuator) A; this cradle A' can typically be moved/positioned in X, Y, Z, and can also often be rotated about X and/or Y (see the depicted Cartesian coordinate system). Such positioning allows different parts of the sample holder S to be irradiated/imaged/inspected by the electron beam traveling along axis B', and also allows the sample holder S to be tilted as part of a tomographic measurement series (sinogram acquisition), for example; in principle, it also allows scanning motion to be performed, as an alternative to beam scanning.

The (focused) electron beam B traveling along axis B' will interact with (specimens suspended in) film 29 (see FIGS. 1, 2E) on the sample holder S in such a manner as to cause various types of "stimulated" radiation flux to emanate from film 29, including (for example) secondary electrons, backscattered electrons, X-rays and optical radiation (cathodoluminescence). If desired, one or more of these radiation types can be detected using detector 22. However, in addition/alternatively, one can study electrons that traverse (pass through) the film 29, emerge (emanate) from it and continue to propagate (substantially, though generally with some deflection/scattering) along axis B'. Such a transmitted electron flux enters an imaging system (combined objective/projection lens) 24, which will generally comprise a variety of electrostatic/magnetic lenses, deflectors, correctors (such as stigmators), etc. In normal (non-scanning) TEM mode, this imaging system 24 can focus the transmitted electron flux onto a fluorescent screen 26, which, if desired, can be retracted/withdrawn (as schematically indicated by arrows 26') so as to get it out of the way of axis B'. An image (or diffractogram) of (part of) the (specimens suspended in) film 29 will be formed by imaging system 24 on screen 26, and this may be viewed through viewing port 28 located in a suitable part of a wall of enclosure E. The retraction mechanism for screen 26 may, for example, be mechanical and/or electrical in nature, and is not depicted here.

As an alternative to viewing an image on screen 26, one can instead make use of the fact that the depth of focus of the electron flux emerging from imaging system 24 is generally quite large (e.g. of the order of 1 meter). Consequently, various other types of analysis apparatus can be used downstream of screen 26, such as:

TEM camera 30. At camera 30, the electron flux can form a static image (or diffractogram) that can be processed by controller C and displayed on a display device (not depicted), such as a flat panel display, for example. When not required, camera 30 can be retracted/withdrawn (as schematically indicated by arrows 30') so as to get it out of the way of axis B'.

STEM recorder 32. An output from recorder 32 can be recorded as a function of (X,Y) scanning position of the beam B on the film 29, and an image can be constructed that is a "map" of output from recorder 32 as a function of X,Y. Recorder 32 can comprise a single pixel with a diameter of e.g. 20 mm, as opposed to the matrix of pixels characteristically present in camera 30. Moreover, recorder 32 will generally have a much higher acquisition rate (e.g. $10^6$ points per second) than camera 30 (e.g. $10^2$ images per second). Once again, when not required, recorder 32 can be retracted/withdrawn (as schematically indicated by arrows 32') so as to get it out of the way of axis B' (although such retraction would not be a necessity in the case of a donut-shaped annular dark field recorder 32, for example; in such a recorder, a central hole would allow beam passage when the recorder was not in use).

As an alternative to imaging using camera 30 or recorder 32, one can also invoke spectroscopic apparatus 34, which could be an EELS module, for example.

It should be noted that the order/position of items 30, 32 and 34 is not strict, and many possible variations are conceivable. For example, spectroscopic apparatus 34 can also be integrated into the imaging system 24.

Note that the controller (computer processor) C (which may have a unitary or composite structure, as desired) is connected to various illustrated components via control lines (buses) C'. This controller C can provide a variety of functions, such as synchronizing actions, providing setpoints, processing signals, performing calculations, and displaying messages/information on a display device (not depicted). The skilled artisan will understand that the interior of the enclosure E does not have to be kept at a strict vacuum; for example, in a so-called "Environmental TEM/STEM", a background atmosphere of a given gas is deliberately introduced/maintained within the enclosure E. The skilled artisan will also understand that, in practice, it may be advantageous to confine the volume of enclosure E so that, where possible, it essentially hugs the axis B', taking the form of a small tube (e.g. of the order of 1 cm in diameter) through which the employed electron beam passes, but widening out to accommodate structures such as the source 4, supporting device H, screen 26, camera 30, recorder 32, spectroscopic apparatus 34, etc.

The invention claimed is:

1. A method of preparing a sample for study in a charged-particle microscope, comprising:
    providing a substantially planar sample holder having opposed faces substantially parallel to one another, comprising at least one aperture that connects said faces and across which a membrane has been mounted, which membrane comprises at least one perforation;
    spanning a film of aqueous liquid across said perforation, which liquid comprises at least one study specimen suspended therein;
    prior to said spanning step, placing a blotting sheet of blotting material in intimate contact with a first surface of said membrane, at a side distal from said sample holder;
    depositing said aqueous liquid through said aperture and onto a second surface of said membrane, opposite said first surface; and
    subsequently removing said blotting sheet from said membrane.

2. A method according to claim 1, wherein:
    said membrane comprises multiple perforations and is mounted across a plurality of said apertures such that at least one perforation occurs within each aperture of said plurality;
    said depositing is localized, and is confined to a particular zone of the sample holder, which zone comprises a subset of said plurality of apertures.

3. A method according to claim 2, wherein, before removing said blotting sheet, said depositing is performed in at least two different zones of the sample holder, whereby:
    a first aqueous liquid is deposited through a first aperture in a first of said zones;
    a second aqueous liquid, different from said first aqueous liquid, is deposited through a second aperture in a second of said zones.

4. A method according to claim 1, wherein said depositing is performed using a dispensing device selected from the group comprising a contactless dispenser and a touch-off dispenser.

5. A method according to claim 1, wherein at least said depositing is performed in a space having a relative humidity of at least 95%.

6. A method according to claim 1, wherein the blotting sheet is pre-wetted prior to said depositing step.

7. A method according to claim 1, wherein, after removing said blotting sheet, said sample holder is plunged into a cryogenic coolant.

8. A method of examining a sample in a charged-particle microscope, which microscope comprises:
    a supporting device, for supporting a sample holder on which the sample is mounted;
    a charged-particle source, for producing a beam of charged particles;
    an illuminator, for directing said beam so as to irradiate the sample; and
    a detector arrangement, for detecting a flux of output radiation emanating from the sample in response to said irradiation,
the method comprising:
    placing the sample on said supporting device; and
    prior to the sample being placed on said supporting device, preparing the sample using a method as claimed in claim 1.

9. A method according to claim 8, wherein said microscope is provided with a cooling device for maintaining said sample holder at a cryogenic temperature while it is on said supporting device.

10. An apparatus for examining a sample in a charged particle microscope, comprising:
    a substantially planar sample holder having opposed faces substantially parallel to one another, comprising at least one aperture that connects said faces and across which a membrane has been mounted, which membrane comprises at least one perforation;
    a charged particle source, for producing a beam of charged particles,
    an illuminator, for directing said beam so as to irradiate the sample,
    a detector arrangement, for detecting a flux of output radiation emanating from the sample in response to said irradiation;
    one or more dispensers for depositing liquid;
    a controller for synchronizing the actions of the apparatus for:
        placing a blotting material in contact with a first surface of the sample;
        spanning a film of aqueous liquid across a perforation in the membrane, which liquid comprises at least one study specimen suspended therein, by depositing said aqueous liquid through said aperture and onto a second surface of said membrane, opposite said first surface; and
        subsequently removing said blotting material from said membrane.

11. The apparatus of claim 10, wherein the aqueous liquid is deposited by a contactless dispenser.

12. The apparatus of claim 11, wherein the contactless dispenser is an inkjet-type dispenser.

13. The apparatus of claim 11, wherein the contactless dispenser is a continuous flow dispenser or volumetric dispenser.

14. The apparatus of claim 10, wherein the aqueous liquid is deposited by a touch-off dispenser.

15. The apparatus of claim 10, wherein the apparatus comprises more than one dispenser, and each dispenser dispenses a different aqueous liquid.

16. The apparatus of claim 10, wherein a single dispenser dispenses multiple different aqueous liquids.

17. The apparatus of claim 10, wherein the membrane comprises multiple perforations and is mounted across a plurality of said apertures such that at least one perforation occurs within each aperture of said plurality; and the deposition of liquid is localized and confined to a sample zone of the sample holder, the sample zone being a subset of said plurality of apertures.

18. The apparatus of claim 17, wherein the sample holder defines multiple sample zones, and the controller synchronizes the action of depositing different aqueous liquids into one or more of the sample zones.

\* \* \* \* \*